United States Patent [19]

Marini et al.

[11] Patent Number: 4,491,008
[45] Date of Patent: Jan. 1, 1985

[54] METHOD OF ULTRASONIC MEASUREMENT OF THE RATIO OF THE VOLUME OF GAS PRESENT IN AN ENCLOSURE CONTAINING A LIQUID-GAS MIXTURE TO THE TOTAL VOLUME OF THE ENCLOSURE

[75] Inventors: Jean Marini, Marly Le Roi; Jean-Paul Heinrich, Champs-sur-Marne, both of France

[73] Assignee: Framatone & Cie, Courbevoie, France

[21] Appl. No.: 467,567

[22] Filed: Feb. 17, 1983

[30] Foreign Application Priority Data

Feb. 19, 1982 [FR] France .................. 82 02750

[51] Int. Cl.³ .............................................. G01N 29/02
[52] U.S. Cl. .................................. 73/19; 73/290 V; 376/250
[58] Field of Search .............. 73/19, 61 R, 290 V; 376/247, 249, 250, 252; 367/908

[56] References Cited

U.S. PATENT DOCUMENTS

| 3,100,885 | 8/1963 | Welkowitz et al. | 73/290 V |
| 3,744,301 | 7/1973 | Arave | 73/61 R |
| 3,974,683 | 8/1976 | Martin | 73/61 R |

*Primary Examiner*—Stephen A. Kreitman
*Attorney, Agent, or Firm*—Pollock, Vande Sande & Priddy

[57] ABSTRACT

The invention relates to a method of ultrasonic measurement of the ratio of the volume of gas present in an enclosure containing a diphase liquid-gas mixture to the volume of the enclosure, or void coefficient. Waves at different frequencies are propagated through the fluid filling the enclosure (1). The propagation times of the waves are measured and the difference between these propagation times is calculated. If the propagation times are identical, it is deduced that all the gas is in the form of a layer surmounting the liquid. The void coefficient is determined from the propagation velocities of the ultrasounds in the gas and the liquid and from the measured propagation time. If the propagation times are different, a part of the gas is in the form of bubbles in the liquid, the void coefficient due to the gas surmounting the liquid and the void coefficient due to the gas bubbles in the liquid are determined separately. The total void coefficient is determined by adding the two values obtained. The void coefficient due to the gas surmounting the liquid may be determined by virtue of the waves reflected by the gas-liquid interface. The void coefficient due to the gas bubbles is determined by virtue of the relationships existing between the velocity of the ultrasounds and the frequency of the waves, according to the pressure and the void coefficient. The invention is applicable to the measurement of the void coefficient in a pressurized water nuclear reactor after an accident.

5 Claims, 6 Drawing Figures

METHOD OF ULTRASONIC MEASUREMENT OF THE RATIO OF THE VOLUME OF GAS PRESENT IN AN ENCLOSURE CONTAINING A LIQUID-GAS MIXTURE TO THE TOTAL VOLUME OF THE ENCLOSURE

The invention relates to a method of ultrasonic measurement of the ratio of the volume of gas present in an enclosure containing a diphase liquid-gas mixture to the total volume of the enclosure or void coefficient, the gas undissolved in the liquid assuming the form of a layer surmounting the liquid and/or the form of bubbles distributed in the liquid.

The primary circuit of pressurised water nuclear reactors, when they are in service, contains water at a very high pressure of the order of 155 bars and at a temperature of the order of 310° C.

In the case of a rupture in a pipe of the primary circuit, the pressure of this water falls very rapidly and an at least partial vaporisation of the primary water occurs. The safety injection circuit of the reactor is then used to prevent excessive heating of the core or of the other parts of the primary circuit.

During the moments following a rupture in the primary circuit, it is extremely important to evaluate the effect of the safety measures adopted and in particular the effect of the injection of water into the primary circuit by measuring the proportion of steam present in the cooling fluid.

For example, it is important to know the ratio of the volume of steam contained in a pipe of the primary circuit to the total volume of that pipe, after a rupture. This ratio, called the void coefficient, can of course evolve very rapidly after the rupture, as a function of the seriousness of that rupture and of the efficacity of the safety measures automatically triggered or adopted by the operator in charge of the station.

Hitherto, no extremely rapid and extremely reliable method of determining the void coefficient in a part of the primary circuit of a nuclear reactor was known.

Indeed, the difficulty of this measurement is increased by the fact that the steam produced in the primary circuit can assume the form of bubbles distributed within the primary water, in the form of a layer of steam surmounting the unvaporised water, or alternatively in both forms simultaneously.

It is generally considered that if the vaporisation continues in the primary circuit until it becomes total, in the course of time successive phases will be found in which the steam is at first in the form of bubbles distributed in the water, then in the form of bubbles distributed in the water and in the form of a layer surmounting the water/steam bubbles mixture, and then in the form of an increasingly thick layer of steam surmounting the water no longer containing gas bubbles.

It is therefore extremely difficult to imagine a method of measuring the void coefficient which permits all these different cases to be dealt with.

More generally speaking, when a gas is introduced into an enclosure which normally contains only a liquid, this gas being in the form of bubbles distributed in the liquid, in the form of a layer surmounting the liquid or in both these forms simultaneously, it may be extremely desirable to know the ratio of the volume of gas to the total volume of the enclosure, e.g. in order to know the size of a leak and to determine the actions to be taken following that incident.

On the other hand, it is entirely out of the question to have direct access to the fluid inside the enclosure, since this fluid is generally at very high pressure and at very high temperature.

On the other hand, the use of ultrasonic waves in order to determine various physical parameters of a fluid in an enclosure or a pipe, by measuring attenuation or propagation time, is known. However, no method is known which permits a determination of the void coefficient from the attenuation measurement or propagation time measurement of ultrasound.

SUMMARY OF THE INVENTION

It is therefore the aim of the invention to propose a method of ultrasonic measurement of the ratio of the volume of gas present in an enclosure containing a diphase liquid-gas mixture to the total volume of the enclosure, or void coefficient, the gas undissolved in the liquid assuming the form of a layer surmounting the liquid and/or the form of bubbles distributed in the liquid, this method being required to permit an extremely rapid determination of the void coefficient, whatever the form assumed by the gas inside the enclosure.

With this aim:

- an ultrasonic wave at a first frequency is propagated along a path of low inclination with reference to a vertical section and crossing the enclosure,
- an ultrasonic wave at a second frequency is propagated along a path close to the path of the first wave,
- the propagation times of the first and of the second waves through the fluid filling the enclosure are measured,
- the pressure or a physical parameter directly related to the pressure of the fluid filling the enclosure is measured,
- the propagation times of the first and of the second waves are compared,
- in the case where the propagation times are identical, all the gas in the enclosure being in the form of a layer surmounting the liquid and in equilibrium therewith, the void coefficient in the enclosure is determined from the propagation velocities of the ultrasounds in the gas and in the liquid at the relevant pressure, previously determined, and from the propagation time of the waves in the stratified fluid filling the enclosure,
- in the case where the propagation times are different, at least a part of the gas being in the form of bubbles distributed in the liquid and in equilibrium therewith:
- the presence or absence of a reflected wave is determined from the ultrasonic waves crossing the enclosure,
- in the case where this reflected wave is present, the propagation time in the gas of this wave reflected from the gas-liquid interface present in the enclosure is measured, and the void coefficient due to the layer of gas surmounting the liquid in the enclosure is determined from this propagation time and from the velocity of the ultrasounds in the gas at the relevant pressure, previously determined,
- the propagation velocity of at least one of the two waves at different frequencies through the fluid constituted by the liquid containing the gas bubbles is calculated,
- from this velocity, and using the relationships existing between the pressure, the frequency of the ultrasonic waves and the propagation velocity of the ultrasonic waves in the liquid containing the gas bubbles, previously determined, the void coefficient due to the gas bubbles distributed in the liquid is determined, and the total void coefficient is determined by adding the void coefficient due to the gas layer and the void coefficient due to the bubbles distributed in the liquid.

According to a variant, in the case where the propagation times of the ultrasonic waves are different, at least part of the gas being in the form of bubbles distributed in the liquid and in equilibrium therewith, the void coefficient is determined without having recourse to capturing waves reflected by the gas-liquid interface.

For this purpose, use is made of the relationships existing between the height of a possible layer of gas above the liquid containing the gas bubbles, the velocities of the ultrasonic waves in the gas and the liquid-gas bubbles mixture and the propagation times of the waves through the fluid filling the enclosure, and also the relationship between the velocities of the waves in the liquid-gas bubbles mixture for each of the frequencies, previously determined by calibration, as a function of the void coefficient due to the gas bubbles. From these relationships, the void coefficient due to the gas bubbles distributed in the liquid, the height of gas in the enclosure and the void coefficient due to the gas surmounting the liquid are determined.

The total void coefficient is then determined by adding the void coefficient due to the gas surmounting the liquid and the void coefficient due to the gas bubbles distributed in the liquid.

According to another variant of the method according to the invention, in the case where all the gas is in the form of bubbles distributed in the liquid:

the ratio of the difference of the propagation times of the waves at different frequencies to the difference of the logarithms of the frequencies is calculated, and the void coefficient in the enclosure is determined by comparing the ratio obtained with the gradient of the curves representing the variations of the propagation velocity of the waves as a function of the frequency, according to the void coefficient and the fluid pressure, which curves are previously determined by calibration.

In order to make the invention fully understood, two embodiments of the method according to the invention will now be described by way of non-limiting examples in the case of an enclosure containing partly vaporised pressurised water, the steam possibly assuming the form of a layer surmounting the liquid and/or of gas bubbles distributed in the liquid, and in the case of a pipe containing pressurised water and steam in the form of gas bubbles distributed in that pressurised water.

DESCRIPTION OF THE PREFERRED EMBODIMENT

Figure 1:
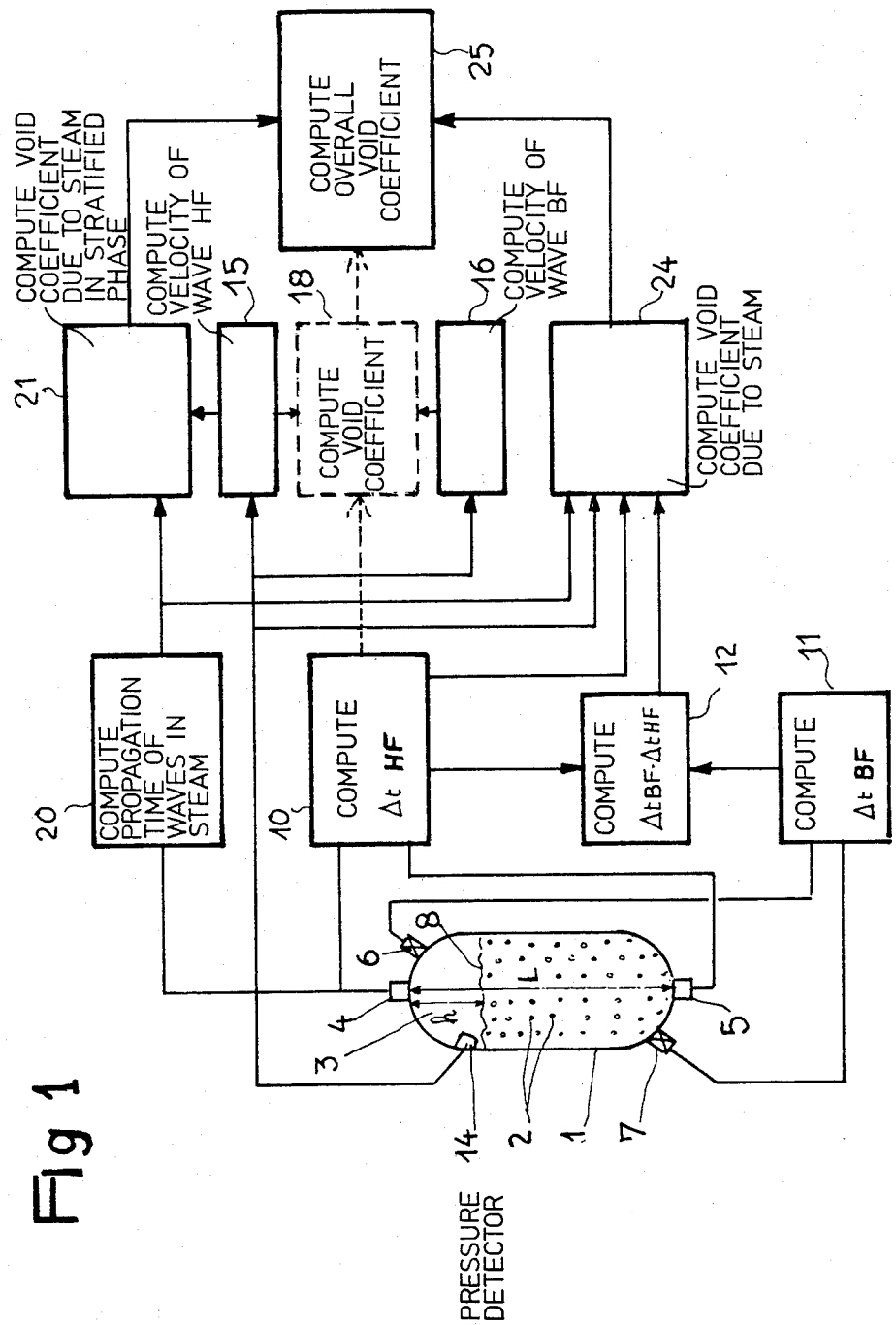
FIG. 1 illustrates schematically an installation permitting the determination of the void coefficient in an enclosure.

In FIG. 1, we see an enclosure 1 containing water and steam, the latter being both in the form of bubbles 2 distributed in the water, and in the form of a layer 3 surmounting the unvaporised water.

This distribution of the water and of the steam assumes this form, e.g. in a tank orginally containing pressurised water which has undergone partial depressurisation and vaporisation.

This represents the second stage of the vaporisation.

In the first stage, the steam is solely in the form of bubbles distributed within the liquid, which is not surmounted by any layer of steam.

In a third stage, the steam bubbles distributed in the water disappear and one is confronted by a certain quantity of water surmounted by a stratified layer of steam. The layer of steam increases up to the total vaporisation of the water.

Transducers 4, 5, 6 and 7 are arranged on the enclosure and on either side thereof in the vertical direction and in an adjacent direction, permitting ultrasonic waves to be transmitted and captured through the fluid filling the enclosure 1. Between the transducers 4 and 5, the rectilinear distance over which the ultrasonic waves are propagated is practically identical to the length over which the waves are propagated between the transducers 6 and 7.

The transducers 6 and 7 permit the transmission and the reception of a low-frequency ultrasonic wave, of the order of 1 KHz. The transducers 4 and 5 permit the transmission and the reception of high-frequency ultrasonic waves of the order of 1 MHz.

The transducer 6 also permits the capture on return of the ultrasonic waves transmitted in the vertical direction, after reflection from the top level 8 of the water containing the bubbles.

Computer units 10 and 11 permit a determination of the propagation time in the fluid filling the enclosure, of the high-frequency waves and the low-frequency waves respectively.

A computer 12 permits the calculation of the difference between the propagation times of the low-frequency waves and of the high-frequency waves.

The propagation velocity of the ultrasonic waves in a homogeneous medium, such as water and steam, is independent of the frequency of these waves.

On the other hand, these velocities are variable as a function of the pressure of the fluid in which they are propagated.

A pressure detector 14 inside the tank 1 permits the equilibrium pressure of the steam and of the water in this tank to be determined. This pressure corresponds to a quite definite value of the temperature of the fluid in the enclosure 1.

When a wave is propagated in water containing steam bubbles, its propagation velocity depends upon its frequency and increases with that frequency.

If the difference of the propagation times $\Delta t\ BF - \Delta t\ HF$ is zero, it may be concluded that the steam contained in the tank 1 is entirely in the form of a layer surmounting the unvaporised pressurised water.

The void coefficient in the tank 1 may then be determined in two different ways.

Starting from the value of the pressure measured by the detector 14, computer units 15 and 16 permit a determination of the velocity of the ultrasounds in the steam and in the water at the pressure measured by the detector 14.

From these values of the velocities of the ultrasounds and of the propagation time calculated e.g. by the computer unit 10, it is possible to determine, by virtue of a computer unit 18, the void coefficient due to the steam surmounting the water in the enclosure 1.

In fact, the length of the path of the ultrasounds in the steam which is connected in a simple way to the void coefficient in the enclosure can be determined extremely easily from the propagation time of the waves and from the velocities of the ultrasounds in the steam and in the water at the relevant pressure.

In the case where the high and low-frequency propagation times are equal, the overall void coefficient is equal to the void coefficient due to the steam in stratified phase obtained by means of the computer unit 18.

A second way of obtaining the void coefficient is to capture, by means of the transducer 4, the ultrasonic waves reflected by the surface 8 of the water, after a path representing twice the height h of the steam layer above the water in the enclosure 1.

A computer unit 20 permits determination of the propagation time of the ultrasonic waves in the steam, the length of the path of these ultrasonic waves being equal to 2 h.

The computer unit 21 permits determination of the void coefficient due to the steam stratified phase above the water, from the propagation time of the waves in the steam supplied by the computer unit 20 and from the velocity of the ultrasounds in the steam at the relevant pressure supplied by the computer unit 15. Subject to the precision of measurement, this value is equal to the value obtained by virtue of the computer unit 18.

Figure 2:
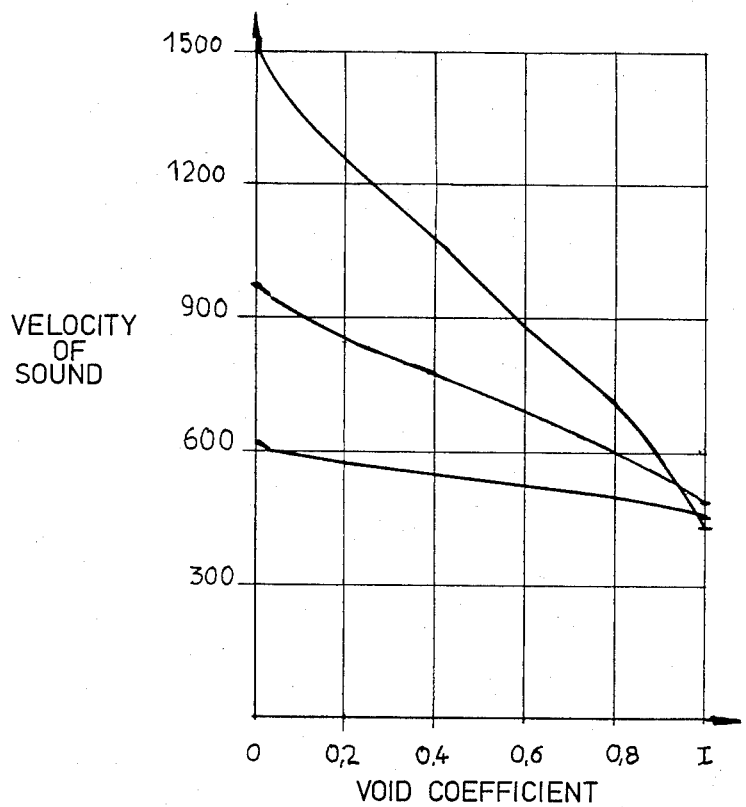
FIG. 2 is an illustration of the variations of the velocity of sound in a stratified water-steam mixture, as a function of the void coefficient, according to the pressure of the water-steam mixture.

FIG. 2 illustrates the variations of the velocity of sound in a stratified water-steam mixture filling a horizontal cylindrical pipe as a function of the void coefficient and for different pressures of the fluid filling the pipe corresponding to quite definite temperatures of that fluid.

In this case, it is sufficient to know the propagation velocity of the ultrasonic waves (or the propagation time in the pipe) and the pressure of the fluid in order to determine with certainty the void coefficient in the pipe.

A computer unit having in its memory the equations of the curves such as illustrated in FIG. 2, and for a sufficient number of pressures to permit extrapolation, leads to the immediate determination of the void coefficient from the propagation time of the ultrasonic waves in the pipe containing water surmounted by steam.

In the case where the propagation times of the low frequency waves and of the high-frequency waves are different, it is deduced that the steam is at least partly in the form of bubbles distributed in the unvaporised water.

In this case, it is necessary to determine whether one is dealing with water containing steam bubbles surmounted by steam as illustrated in FIG. 1, or with water containing bubbles occupying the entire volume of the enclosure 1.

The presence of a liquid-steam interface 8 may be determined by capturing the wave possibly reflected from the surface 8, by virtue of the transducer 4.

The computer unit 20 already described permits calculation of the propagation time of waves in the steam, along a forward and return path between the transducer 4 and the surface 8.

The knowledge of the velocity of the ultrasounds in the steam at the relevant pressure supplied by the computer unit 15 permits determination of the height of steam h in the enclosure, that is to say the void coefficient in that enclosure due to the steam layer surmounting the unvaporised water containing steam bubbles.

Figure 3A:
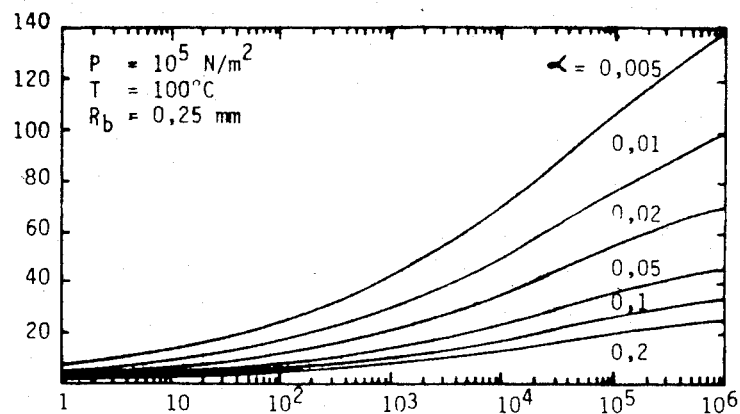
FIG. 3 illustrates, for three different values of the pressure and of the temperature of the pressurised water, the variations of the velocity of sound as a function of the frequency of an ultrasonic wave propagated in water containing steam bubbles, according to the void coefficient.
Figure 3B:
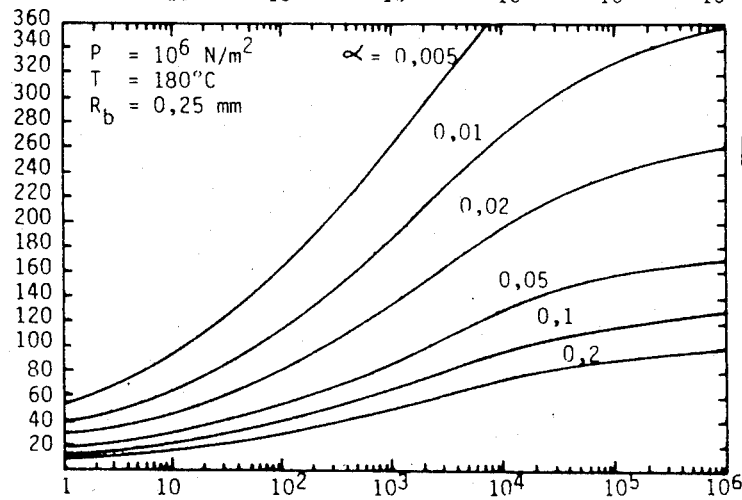
Figure 3C:
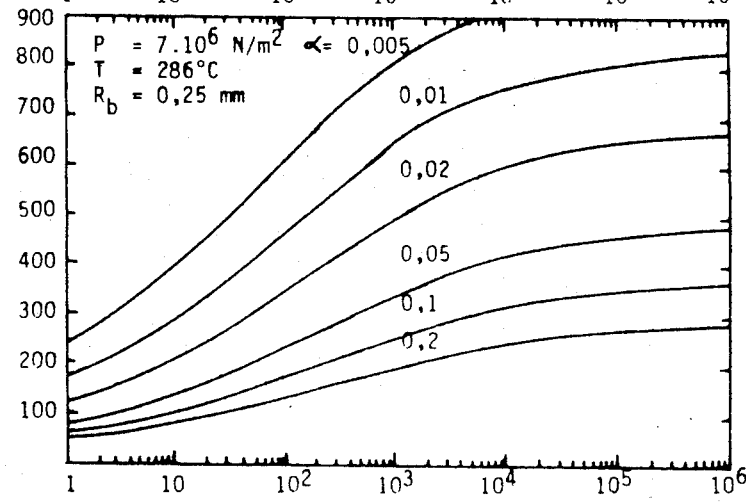

In FIG. 3, we see a set of curves representing the variations of the velocity of ultrasonic waves as a function of the frequency, for different values of the void coefficient and for different values of the pressure of the fluid, in the case where this fluid is constituted by water containing gas bubbles distributed in the mass of water.

Such curves can be memorised in large quantities in a computer unit 24 receiving as input data the propagation time of the high-frequency waves determined by the computer unit 10, the propagation time of the waves in the steam, coming from the computer unit 20, and the pressure of the fluid filling the enclosure 1. From these input data and from the relationships or graphs memorised, the computer unit 24 permits determination of the velocity of the high-frequency waves in the water containing steam bubbles and the void coefficient due to the steam in the form of bubbles.

This void coefficient is added to the void coefficient due to the steam in stratified phase calculated by the unit 21, in a computer 25.

The computer 25 can then give the value of the overall void coefficient in the enclosure 1.

Processing by the computer unit 24 is tripped when a difference between the propagation times of the low and high-frequency waves is detected at the level of the computer unit 12.

It is also possible to determine the void coefficient due to the stratified steam and due to the steam bubbles without having recourse to a measurement of the propagation time of a wave reflected from the surface 8 of the pressurised water.

For this purpose a computer unit is used having in its memory the curves of relationships between the propagation velocity of the waves and the frequency in a mixture of water and of steam bubbles, according to the pressure and according to the void coefficient. Such curves as illustrated in FIG. 3. In fact, if L designates the length of the path of the waves throughout the crossing of the tank 1, the following relationships may be written:

$$\Delta t \, BF = (h/CV) + (L-h)/C_1(BF)$$

$$\Delta t \, HF = (h/CV) + (L-h)/C_1(HF)$$

CV being the velocity of the ultrasonic waves in the steam at the relevant pressure, and $C_1(BF)$ and $C_1(HF)$ the velocities of the ultrasonic waves in the liquid containing the bubbles at the relevant pressure, for the low-frequency and high-frequency waves respectively.

Memorising the relationships of curves illustrated in FIG. 3 in the computer unit permits a relationship between $C_1(BF)$ and $C_1(HF)$ to be introduced.

The input data into the computer unit are the propagation times $\Delta t \, BF$ and $\Delta t \, HF$, the pressure and the propagation velocity of the ultrasounds in the steam, which permits determination of the value of the height h of the steam layer and of the void coefficient due to the bubbles of steam in the water.

Those values are determined by iteration, using the curves memorised.

From a knowledge of the height h, the void coefficient due to the stratified steam is deduced by virtue of the computer unit, and the overall void coefficient is found by adding this void coefficient due to the stratified steam and the void coefficient due to the steam bubbles in the water.

However, preference is given to a method of determination using the reflected waves, which permit better discrimination between the different cases and more precise determination of the void coefficients.

Figure 4:
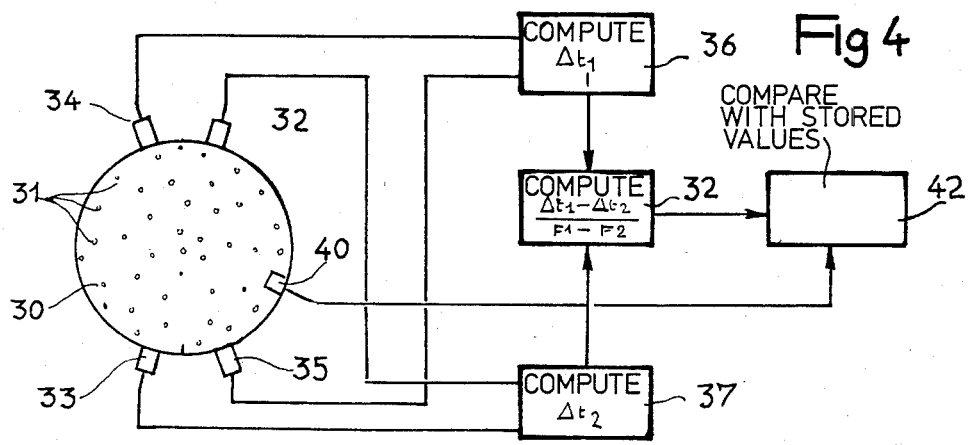
FIG. 4 illustrates, schematically, an installation for measuring the void coefficient in a pipe containing pressurised water containing steam bubbles.

In FIG. 4, we see the cross-section 30 of a large-diameter pipe such as a primary circuit pipe of a pressurised water reactor, inside which an initial vaporisation has occurred. Steam bubbles 31 have formed in the pressurised water, but no stratified layer of steam has yet been able to form.

Under these conditions, a simplified apparatus for the measurement of the void coefficient can be used.

This apparatus comprises two pairs of transducers 32, 33 and 34, 35 arranged diametrally opposite one another on the pipe 30.

The pair of transducers 32, 33 permits the transmission and the capture of an ultrasonic wave at a first frequency, whereas the pair of transducers 34, 35 permits the transmission and capture of an ultrasonic wave at a second frequency.

The propagation times of these ultrasonic waves in the fluid filling the pipe 30 are calculated by computer units 36 and 37. A computer unit 38 permits calculation of the ratio $(\Delta t1 - \Delta t2)/(\text{Log } F1 - \text{Log } F2)$ between the difference of the propagation times of the waves and the difference of the logarithms of the frequencies. A pressure detector 40 is arranged inside the pipe 30 to supply a signal representative of the pressure of the fluid filling the pipe 30 to a computer unit 42 likewise receiving from the computer unit 38 a signal representative of the ratio of the differences of transit time to the difference of the frequencies of the ultrasonic waves.

The computer unit 42 has, recorded in its memory, the relationships between velocity of ultrasonic waves and frequency, according to the various void coefficients and according to the various pressures, determined by calibration and as illustrated, e.g. in FIG. 3.

As a function of the pressure measured by the detector 40 in the pipe 30, the computer unit 42 permits a comparison of the ratio $(\Delta t1 - \Delta t2)/(\text{Log } F1 - \text{Log } F2)$ with the gradient of the curves giving the variation of the velocity of sound as a function of the frequency.

The frequencies F1 and F2 are relatively close, so that the comparison of the gradients and of the ratio is made close to one of the frequencies or to a mean frequency. This permits determination of the void coefficient since, as may be seen in FIG. 3, the gradients of the curves vary strongly with the void coefficient.

The measurement of the void coefficient can therefore be effected very rapidly by using relatively close frequencies for the two ultrasonic waves.

The paths of these waves may deviate strongly from the vertical and form a large angle between them. In fact, the distribution of the bubbles in the fluid is substantially homogenous.

This simplified method of determining the void coefficient is extremely useful in the early stages following a rupture in the primary circuit of a pressurised water reactor.

In fact, the vaporisation of the water commences by the appearance of gas bubbles within the pressurised water.

This is moreover the phase in which it is imperative to know the void coefficient very precisely and rapidly in order to be able to remedy very rapidly the effects of an accidental rupture in the primary circuit.

In the majority of cases, the safety systems are so designed that it is entirely improbable that an accident could lead to a vaporisation with a stratified layer of steam.

It will be seen that the advantages of the method according to the invention are to permit a very rapid and very precise determination of the void coefficient in an enclosure or a pipe containing pressurised water, irrespective of the state in which the steam occurs.

More generally, the device may permit determination of the proportion of gas in a liquid contained in an enclosure or a pipe.

The invention is not limited to the embodiments which have been described; on the contrary, it comprises all variants thereof. Thus reflected waves may be used for the measurement of the void coefficient due to a stratified layer of gas and in order to determine the presence of a gas-liquid interface in the enclosure, or on the contrary, a method may be used which does not have recourse to echography.

Instead of a pressure measurement in the enclosure, a measurement of another parameter related to the pressure of the fluid, e.g. the temperature, may be performed.

In the case where the enclosure contains a liquid having gas bubbles in suspension, the frequencies of the ultrasonic waves and the paths of the latter within the fluid may be chosen freely.

The method according to the invention is applicable not only in the case of determining the void coefficient in the primary circuit of a pressurised water nuclear reactor, but also in the case of any pressurised liquid capable of vaporising, and even in the case of any liquid which may contain a gas in a variable proportion.

We claim:

1. A method of ultrasonic measurement of the ratio of the volume of gas present in an enclosure containing a diphase liquid-gas mixture to the total volume of the enclosure, the gas undissolved in the liquid assuming the form of a layer surmounting the liquid and/or the form of bubbles distributed in the liquid comprising:

propagating an ultrasonic wave at a first frequency along a path of low inclination with reference to a vertical section and crossing the enclosure, propagating an ultrasonic wave at a second frequency along a path close to the path of the first wave, measuring the propagation times of the first and of the second waves through the fluid filling the enclosure, measuring the pressure or a physical parameter directly related to the pressure of the fluid filling the enclosure, comparing the propagation times of the first and of the second waves, in the case where the propagation times are identical, all the gas in the enclosure being in the form of a layer surmounting the liquid and in equilibrium therewith, the void coefficient in the enclosure is determined from the propagation velocities of the ultrasound waves in the gas and in the liquid at the relevant pressure, previously determined, and from the propagation time of the waves in the stratified fluid filling the enclosure, in the case where the propagation times are different, at least a part of the gas being in the form of bubbles distributed in the liquid and in equilibrium therewith:

determining the presence or absence of a reflected wave from the ultrasonic waves crossing the enclosure, in the case where a reflected wave is present, the propagation time in the gas of the wave reflected from the gas-liquid interface present in the enclosure is measured, and the void coefficient due to the layer of gas surmounting the liquid in the enclosure is determined from this propagation time and from the velocity of the ultrasounds in the gas at the relevant pressure, previously determined, calculating the propagation velocity of at least one of the two waves at different frequencies through the fluid constituted by the liquid containing the gas bubbles, determining from this velocity, and the relationships existing between the pressure, the frequency of the ultrasonic waves and the propagation velocity of the ultrasonic waves in the water containing the gas bubbles, the void coefficient due to the gas bubbles distributed in the liquid, and determining the total void coefficient by adding the void coefficient due to the gas layer and the void coefficient due to the bubbles distributed in the liquid.

2. The method of measurement according to claim 1, wherein when the propagation times of the two waves are identical, all the gas in the enclosure is determined to be in the form of a layer surmounting the liquid and in equilibrium therewith, and a wave reflected by the gas-liquid interface is captured, the propagation time in the gas of this reflected wave is measured, and the void coefficient in the enclosure is determined from this propagation time and from the velocity of the ultrasounds in the gas at the relevant previously determined pressure.

3. The method of measurement according to claim 1, wherein when the propagation times of the two waves are different, at least a part of the gas is determined to be in the form of bubbles distributed in the liquid, and the void coefficient due to the gas bubbles distributed in the liquid, the height of gas in the enclosure, and the void coefficient due to the gas surmounting the liquid are determined from the relationships existing between the height of a possible layer of gas above the liquid containing gas bubbles, the velocities of the ultrasonic waves in the gas and in the liquid-gas bubbles mixture, and the propagation times of the waves through the fluid filling the enclosure, and the relationship between the velocities of the waves in the liquid-gas bubbles mixture at each of the frequencies according to the void coefficient due to the gas bubbles, previously determined during calibration, and the total void coefficient is determined by adding the void coefficient due to the gas surmounting the liquid and the void coefficient due to the gas bubbles distributed in the liquid.

4. A method of ultrasonic measurement of the volume of gas present in an enclosure to the total volume of the enclosure, the gas assuming the form of bubbles distributed in the liquid, comprising:

propagating an ultrasonic wave at a first frequency along a rectilinear path crossing the enclosure, propagating an ultrasonic wave at a second frequency along a second path crossing the enclosure, measuring the propagation times of the first and of the second waves through the fluid filling the enclosure, measuring the pressure or a physical parameter directly related to the pressure of the fluid filling the enclosure, calculating the ratio of the difference of the propagation times of the waves at different frequencies to the difference of the logarithms of the frequencies, determining the void coefficient in the enclosure by comparing the ratio obtained with the gradient of previously determined curves representing the variations of the propagtion velocity of the waves as a function of the frequency, according to the void coefficient and the pressure of the fluid.

5. The method according to any of claims 1 to 4, wherein the void coefficient is measured in the primary circuit of a pressurized water nuclear reactor after an accident accompanied by a depressurization, and at least partial vaporization of the water contained in the enclosure, the gas consisting of steam being formed from the pressurized water.

* * * * *